United States Patent [19]

Chang et al.

[11] Patent Number: 4,983,395

[45] Date of Patent: * Jan. 8, 1991

[54] DEVICE FOR ADMINISTERING AN ACTIVE AGENT TO THE SKIN OR MUCOSA

[75] Inventors: Yunik Chang, Toms River, N.J.; Dinesh C. Patel, Murray; Charles D. Ebert, Salt Lake City, both of Utah

[73] Assignee: TheraTech Inc., Salt Lake City, Utah

[*] Notice: The portion of the term of this patent subsequent to Jul. 18, 2006 has been disclaimed.

[21] Appl. No.: 326,536

[22] Filed: Mar. 21, 1989

Related U.S. Application Data

[63] Continuation-in-part of Ser. No. 119,617, Nov. 12, 1987, Pat. No. 4,849,224.

[51] Int. Cl.⁵ .............................................. A61F 13/02
[52] U.S. Cl. ..................... 424/448; 424/449; 424/447; 424/434
[58] Field of Search ................ 424/448, 449, 434

[56] References Cited

U.S. PATENT DOCUMENTS 4,849,224  7/1989  Chang et al. ............... 424/434

Primary Examiner—Merrell C. Cashion, Jr.
Assistant Examiner—Leon R. Horne
Attorney, Agent, or Firm—Irell & Manella

[57] ABSTRACT

A transdermal drug delivery device comprising a drug formulation-containing reservoir defined by a backing layer and a drug-permeable membrane layer, a peelable inner liner that underlies the reservoir and a portion of the backing/membrane outwardly of the reservoir periphery, an adhesive layer that underlies the inner liner and outwardly extending portions of the membrane/backing layers, and a peelable release liner layer that underlies the adhesive layer with a first permanent heat seal between the backing and the membrane about the perimeter of the reservoir and another concentric peelable (impermanent) heat seal between the membrane and the inner liner positioned underlying and at a radius not less than the first permanent heat seal, the heat seals and peelable barrier layer providing barriers that isolate the drug formulation from the adhesive.

6 Claims, 2 Drawing Sheets

DEVICE FOR ADMINISTERING AN ACTIVE AGENT TO THE SKIN OR MUCOSA

CROSS-REFERENCE TO RELATED APPLICATION

This application is a continuation-in-part of copending U.S. application Ser. No. 119,617 filed 12 Nov. 1987, now U.S. Pat. No. 4,849,224.

TECHNICAL FIELD

This invention is in the field of transdermal/ transmucosal administration of active agents (drugs). More particularly it relates to a device for achieving such administration comprising an active agent-containing reservoir and an adhesive layer for affixing the device to the skin or mucosa in which the adhesive layer is peripheral to the path of the active agent to the skin or mucosa and is protected from degradation by the components of the reservoir by a multiplicity of heat seals.

BACKGROUND OF THE INVENTION

There are many patents describing devices for administering drugs through the skin or mucosa. These devices are commonly in the form of a laminated composite that includes a reservoir layer containing the drug, a pressure sensitive adhesive layer for attaching the composite to the skin, and a backing layer that forms the upper layer of the device. Depending upon the particular drug and drug formulation involved, the reservoir layer may be a matrix in which the drug formulation is dispersed or a layer in the form of a walled container which holds the drug formulation. Container-type reservoirs are often formed as a pocket between the backing layer and a drug-permeable basal membrane through which the drug passes to the skin. The pressure sensitive adhesive layer normally underlies the membrane and the drug also passes through it on its way to the skin.

Devices having container-type reservoirs with underlying pressure sensitive adhesive layers have significant disadvantages when one or more components of the drug formulation that are released from the reservoir to the skin are solvents for the adhesive or otherwise adversely effect the properties of the adhesive as they pass through it to the skin. In such cases those reservoir component(s) cannot be permitted to pass through the adhesive and means must be found to isolate the adhesive from them. Further, in such devices the drug partitions into the adhesive and alters drug release characteristics over prolonged storage. The present invention provides a device design in which the adhesive is peripheral to the path of the drug formulation and is isolated from the drug formulation by a peelable barrier disc and a multiplicity of heat seals between selected layers of the device.

At least one other transdermal drug delivery device design has been proposed which involves an adhesive layer that is peripheral to the path of the drug to the skin. U.S. Pat. No. 4,573,996 describes a device that has both a drug-permeable adhesive layer in the path of the drug and a peripheral drug-impermeable adhesive layer that is not in the path of the drug. The purpose of the peripheral adhesive layer is to provide a site for handling the device which avoids the risks of altering the drug path or contaminating the fingers with drug. FIG. 6 of the patent shows a multi-layer laminated composite composed of (1) a backing layer, (2) a drug permeable membrane underlying the backing that forms with the backing a pocket that serves as a drug-containing reservoir, (3) a drug-permeable adhesive layer directly underlying the membrane, (4) a ring-shaped drug-impermeable adhesive layer adjacent and peripheral to the drug-permeable adhesive layer, and (5) a basal removable protective layer. The combination of a heat seal between the backing and the membrane at the edge of the reservoir and the peripheral drug-impermeable adhesive layer prevents radial or horizontal migration of the drug from the reservoir. This patented device is distinct from the device of the present invention in several respects. The patented device does not involve the problem of keeping drug formulation components isolated from the adhesive layer. In the patented device, the drug passes through the drug-permeable adhesive layer. There is only a single heat seal shown in the patented device. And, the single heat seal is not used to isolate the drug formulation from either adhesive layer.

The present invention is also unique in that it employs two peelable layers, a permanent heat seal and a peelable heat seal in a manner that permits the creation of a peripheral ring of adhesive when the two peelable layers are removed from the device.

DISCLOSURE OF THE INVENTION

The invention is a device for administering an active agent to the skin or mucosa of an individual comprising a laminated composite of:
(a) a backing layer;
(b) an active agent-permeable membrane, the backing layer and membrane defining
(c) a reservoir therebetween that contains a formulation of the active agent, said reservoir having a smaller periphery than the backing layer and membrane such that a portion of the backing layer and membrane extends outwardly of the periphery of the reservoir;
(d) a first peelable active agent formulation-impermeable layer that underlies the reservoir and a portion of said outwardly extending portion of the backing layer and membrane;
(e) an adhesive layer that underlies and covers the first peelable active agent formulation-impermeable layer and said outwardly extending portion of the backing layer and membrane;
(f) a second peelable active agent formulation-impermeable layer that underlies and covers the adhesive layer;
(g) a permanent heat seal about the periphery of the reservoir between the backing layer and the membrane; and
(h) a peelable heat seal between the membrane and the first peelable active agent formulation-impermeable layer located underneath and at a radius not less than that of the permanent heat seal, said permanent and peelable heat seals providing barriers to migration of components of the active agent formulation from the reservoir into the adhesive layer and said first and second peelable active agent impermeable layers being bonded together such that when the second peelable layer is removed from the device the peelable heat seal is broken and the first peelable layer and underlying portion of the adhesive layer is removed therewith.

BRIEF DESCRIPTION OF THE DRAWING

The drawings are not to scale and like parts are referred to by like reference numerals in the various figures.

MODES FOR CARRYING OUT THE INVENTION

Figure 3:
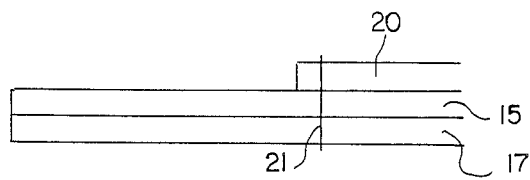
FIGS. 3 and 4 are enlarged sectional views of a portion of other embodiments depicting alternative means for affixing the first and second peelable layers together.
Figure 4:
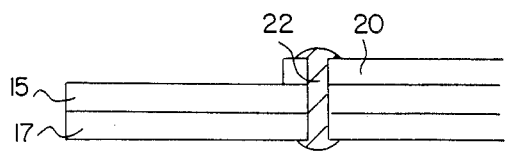

The drawing shows a device, generally designated an embodiment of the invention that is designed to administer a formulation of a drug and/or a permeation enhancer that is a solvent for pressure sensitive adhesives that are commonly used in transdermal delivery devices. Device 11 is designed to place the adhesive out of the path of the enhancer-drug formulation and to prohibit radial or horizontal migration of the drug/enhancer into the adhesive. Device 11 is a laminated composite. The uppermost layer of the composite is a heat-sealable backing film 12 having an inverted, cup-shaped recess 13 that serves as a container or reservoir for a drug-enhancer formulation 14. Underlying the reservoir and all or a portion of the part of the backing layer outwardly of the reservoir is a membrane layer 16 that is permeable to the drug-enhancer formulation. An inner peel sealable liner 20 underlies the membrane layer and extends outwardly of the periphery of the reservoir. The next layer in the composite is a pressure-sensitive adhesive layer 15 that underlies the inner peel sealable liner and the portion of the backing layer that extends outwardly of the edge of the liner. Finally a peelable adhesive release liner layer 17 covers the entire underside of the assembly and forms the basal surface of the device. There are a minimum of two concentric heat seals in the composite. The first is at 18 between the membrane and the backing. It extends completely around the perimeter of the reservoir and forms a permanent seal between the backing film and membrane. The second is at 19 and is between the outer edge of the inner peel sealable liner and the membrane and forms a peelable (impermanent) seal between the membrane and inner liner. It is underneath the first heat seal and at a radius not less than that of the first heat seal. Alternatively, it may be located vertically in line with the first heat seal, but in no event should it lie inwardly of the first heat seal. These seals prevent the drug/enhancer formulation from migrating into the adhesive during storage. After the release liner is removed, the first heat seal prevents such migration during wearing. The width of the seals will usually be in the range of 0.05 cm to 1.0 cm. The peel strength between the adhesive layer and the release liner layer is greater than the force required to break the peelable seal at 19. Thus, when the release liner is peeled from the underside of the assembly the peelable seal is broken and the adhesive layer peripheral to the inner peel sealable liner is cut by the edge of that liner as the release liner and peel sealable liner 20 are removed, leaving the portion of the adhesive between liners 17 and 20 and creating a peripheral ring of adhesive underlying the membrane and backing peripheral to the reservoir (see FIG. 2). Alternatively, the release liner and the inner peel sealable liner may be bonded together (e.g., by permanent adhesive or mechanical bonding) such that removal of the release liner results in simultaneous removal of the inner liner. FIGS. 3 and 4 depict such alternative bonding means. These means are also described in Examples 5 and 6, infra. In FIG. 3 the means is a metal staple 21 that passes vertically through the first peelable layer 20, the underlying adhesive layer 15 and the second peelable (release) layer 17 just inwardly of the edge of layer 20. Correspondingly, in FIG. 4 the means is a plastic rivet 22 that is similarly passed through the three mentioned layers.

When device 11 is placed into use, the release liner layer 17 and inner liner 20 are peeled away from the underside of the device and discarded. This operation directly exposes the undersurfaces of the membrane and the peripheral ring of adhesive layer and the device can be placed on a desired site on the skin or mucosa of the individual to be treated with the active agent.

Figure 1:
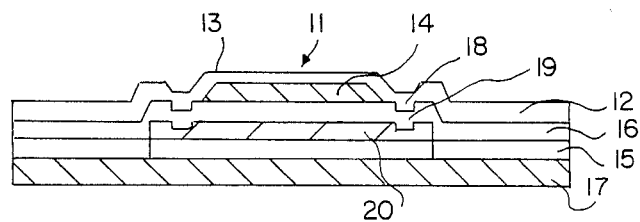
FIG. 1 is an enlarged sectional view of one embodiment of the invention.
Figure 2:
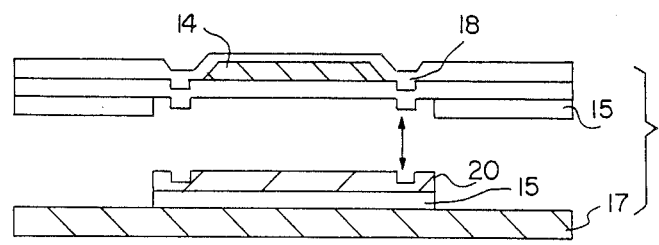
FIG. 2 is an enlarged sectional view of the embodiment of FIG. 1 after the second and first peelable layers have been peeled off the remainder of the embodiment.

In the embodiment shown in FIGS. 1 and 2 the second impermeable heat seal is formed between the membrane and inner liner. It will be appreciated in this regard that additional heat-sealable layers could be included in the device between any of the component layers that are part of the membrane, backing or inner liner, as the case may be.

The invention device is useful when one or more of the components of the active agent formulation is incompatible with available adhesives that are useful for removably attaching elements to the skin or mucosa. The term "incompatible" is intended to mean that through physical and/or chemical interaction of the component(s) with the adhesive the adhesiveness or other desirable properties (e.g., nonirritancy) of the adhesive are significantly destroyed or impaired. The drug itself may be such a component or a carrier, solvent, skin permeation enhancing agent or other additive may be such a component. Also, this design prevents migration of drug into the adhesive which otherwise alters drug release characteristics over prolonged storage.

The backing layer 12 of the device may be composed of a single film or a plurality of films. In any event, its inner surface must be capable of being heat sealed to the membrane. One or more of the films that constitute the layer will be impermeable to components of the drug formulation contained in the reservoir. Examples of materials used as backing layers in transdermal delivery devices that may find use in the present invention are polyethylene, polypropylene, polyethylene vinylacetate, polyethylene terephthalate, and combinations thereof. The layer may include one or more metal layers and/or one or more fibrous layers.

The reservoir pocket in the backing may be formed by vacuum forming or other like methods of forming desired shapes in films.

The term "drug" as used to describe the principal active ingredient of the device intends a biologically active compound or mixture of compounds that has a therapeutic, prophylactic or other beneficial pharmacological and/or physiological effect on the wearer of the device. Examples of types of drugs that may be used in the invention device are antiinflammatory drugs, analgesics, antiarthritic drugs, antispasmodics, antidepressants, antipsychotic drugs, tranquilizers, antianxiety drugs, narcotic antagonists, antiparkinsonism agents, cholinergic agonists, anticancer drugs, immunosuppression agents, antiviral agents, antibiotic agents, appetite suppressants, antiemetics, anticholinergics, antihistamines, antimigraine agents, coronary, cerebral or peripheral vasodilators, hormonal agents, contraceptive agents, antithrombotic agents, diuretics, antihypertensive agents, cardiovascular drugs, and the like. The appropriate drugs of such types are capable of permeating through the skin either inherently or by virtue of treatment of the skin with a percutaneous absorption enhancer. Because the size of the device is limited for patient acceptance reasons, the preferred drugs are those that are effective at low concentration in the blood stream. Examples of specific drugs are steroids such as estradiol, progesterone, norgestrel, levonorgestrel, norethindrone, medroxyprogestrone acetate, testosterone and their esters, nitro-compounds such as nitroglycerine and isosorbide nitrates, nicotine, chlorpheniramine, terfenadine, triprolidine, hydrocortisone, oxicam derivatives such as piroxicam, ketoprofen, mucopolysaccharidases such as thiomucase, buprenorphine, fentanyl, naloxone, codeine, dihydroergotamine, pizotiline, salbutamol, terbutaline, prostaglandins such as misoprostol and enprostil, omeprazole, imipramine, benzamides such as metoclopramine, scopolamine, peptides such as growth releasing factor and somatostatin, clonidine, dihydropyridines such as nifedipine, verapamil, ephedrine, pindolol, metoprolol, spironolactone, nicardipine hydrochloride, calcitriol, thiazides such as hydrochlorothiazide, flunarizine, sydononimines such as molsidomine, sulfated polysaccharides such as heparin fractions and the salts of such compounds with pharmaceutically acceptable acids or bases, as the case may be.

Depending upon the inherent permeability of the skin to the particular drug or drugs being administered by the device, the reservoir may also contain a percutaneous absorption enhancer that increases the permeability of the skin to the drug(s) and is coadministered to the skin. Examples of percutaneous absorption enhancers are those referred to in U.S. Pat. Nos. 3,989,816, 4,316,893, 4,405,616, 4,060,084, and 4,379,454 and *J Pharm Sci* (1975) 64:901–024. The formulation contained in the reservoir may also include solvent(s), gelling agents, stabilizers, and other additives. As indicated previously one or more of these components or a combination of these components is incompatible with the adhesive.

The membrane is permeable to the drug. It may be a "dense" membrane made of a material that is inherently permeable to the components of the reservoir that are to be administered to the skin or mucosa or it may be made of a microporous material whose pores are filled with a drug-permeable material including the drug-enhancer formulation itself. In the case of dense membranes, the component(s) dissolve in the material and diffuse through the material to the skin. In the case of microporous materials the component(s) diffuse through the pores to the skin. The membrane may or may not be a rate-controlling element depending upon the particular drug involved, the permeability of the skin to the drug, and the rate of delivery required to provide therapy. Examples of materials for making dense membranes are given in U.S. Pat. Nos. 3,598,122 and 4,650,484. Examples of materials for making microporous membranes are provided in U.S. Pat. Nos. 3,797,494 and 4,031,894.

The adhesive layer is composed of a pressure sensitive surgical adhesive such as those that are commonly used to affix transdermal drug delivery devices, bandages or other dressings to the skin. Examples of such adhesives are polyisobutene, natural rubber adhesives, acrylic and methacrylic adhesives, and silicone adhesives.

The release liner layer 17 and inner liner 20 may be composed of a single layer or a multiplicity of layers. They should be (1) impermeable to the components of the drug formulation that diffuse through the membrane, (2) heat-sealable in the case of the inner liner, and (3) inherently strippable or peelable or rendered so by techniques such as silicon or fluorocarbon treatment or surface treatment with a seal incompatible layer. An example of a film having such properties is Bertek 4418 Peelable Seal.

The respective components of the device may be formulated and assembled using procedures that are known in the drug formulation, transdermal device, and laminating arts. The shape of the device is not critical, and devices of preformed shapes may be assembled directly or punched, cut, or otherwise formed from large sheets of laminated composite.

The following examples further illustrate the invention. These examples are not intended to limit the invention in any manner.

EXAMPLES

Example 1

A silicone adhesive is prepared by mixing Dow Corning 355 Medical Adhesive with Dow Corning 360 Medical Fluid (10,000 cps) to provide 20% (wt/wt) Medical fluid in the final adhesive. The adhesive/medical fluid mixture is coated onto an Akrosil Biorelease release liner using a 10 mil gap casting knife and the adhesive solvent is evaporated at 80° C. for 15 min to provide a final dry adhesive coating thickness of 0.0025 inches. A peelable heat seal disc (Bertek 4418) is then die cut into a 1.375 inch diameter circular disc which is positioned onto the adhesive surface of above adhesive-coated release liner with the peelable heat seal surface facing outward. A 0.002 inch thick microporous membrane (3M, MSP-61588) is then laminated over the entire surface of the above adhesive/release liner/peelable disc structure to form a membrane/peelable disc/adhesive/release liner laminate (L1).

The backing film (Scotchpak 1012) is pressure formed to provide a 5 cm$^2$ surface area and a 0.4 cc volume circular shaped cup.

A gelled calcitriol/enhancer reservoir formulation is prepared by mixing sufficient amounts of calcitriol and Klucel HF ® with a 67.5%/21.75%/7.5%/3.25% (volume percent) mixture of ethanol/water/glycerine/methyl laurate to provide a 100 ug/ml calcitriol concentration and a 1.5% Klucel HF © gel.

To fabricate a clacitriol system, 0.4 ml of the gelled calcitriol formulation is pipetted onto the microporous membrane surface of the L1 laminate coinciding with the exact center of the peelable disc underlying the membrane. The backing film is then placed over the L1 laminate such that the pre-formed cup on the backing film is situated over the drug/enhancer gel. The backing film is then heat sealed to the L1 laminate using a 0.9934 inch diameter circular heat seal die with a 0.0787 inch width heat sealing zone at 320° C. with 30 PSI pressure for 0.5 seconds. The single heat sealing step creates the permanent heat seal between the backing film and microporous membrane layers, and simultaneously forms the peelable seal between the microporous membrane and the peelable disc directly underneath the permanent seal.

The backing film is then sealed to the microporous membrane in the outer area peripheral to the drug-enhancer reservoir with a heated plate. Finally, a 20 cm$^2$ (overall surface area) calcitriol system is die cut from the heat sealed structure using a steel rule die.

The peel force between the silicone adhesive and the release liner is greater than the force necessary to break the peelable seal between the membrane and the peelable disc. Therefore, when the release liner is peeled the release liner exposing the 5 cm$^2$ microporous membrane drug-enhancer delivery surface area and creating the peripheral adhesive pattern. The in vitro steady state calcitriol skin flux is determined using the methods of Merritt and Cooper (J. Controlled Release 1:161, 1984) to be 1 ug/cm$^2$day.

Example 2

A membrane/peelable disc/adhesive/release liner laminate (L1) is prepared as described in Example 1 using a Scotchpak 1022 release liner in place of the Akrosil Biorelease release liner.

A pindolol-enhancer gel formulation is prepared by mixing adequate quantities of pindolol HCl and Klucel HF® with a mixture consisting of 50%/39%/10%/1% (volume percent) ethanol/water/glycerine/glycerol monooleate to provide a gel with a final pindolol concentration of 65 mg/cc and Klucel level of 1.5% (wt/wt).

The pindolol-enhancer gel is pipetted (0.4 ml) onto the L1 laminate and a Scotchpak 1012 backing film (0.4 ml cup previously formed) is positioned over the laminate. The backing film is then heat sealed to the L1 laminate and a final system is die cut as described in Example 1. When the release liner is peeled from the system, the peel force between the adhesive and release liner is greater than the force necessary to break the peelable seal between the peelable disc and the microporous membrane. The peelable disc is thus removed from the system with the release liner, creating the peripheral adhesive and exposing the drug-enhancer delivery surface area. The in vitro pindolol skin flux from the system is determined using the methods of Merritt and Cooper, supra, to be 33 ug/cm$^2$/hr.

Example 3

An L1 laminate is prepared as described in Example 1 using a polyisobutylene (PIB) adhesive in place of the silicone adhesive and a Daubert C-150 release liner in place of the Akrosil Biorelease release liner. A nicardipine-enhancer gel formulation is prepared by mixing adequate quantities of nicardipine HCl and Klucel HF® with a 65%/10%/20%/5% (volume percent) mixture of ethanol/water/glycerine/glycerol monooleate to provide a final gel with a nicardipine concentration of 150 mg/cc and a Klucel level of 1.5% (wt/wt). A nicardipine transdermal system is then prepared as described in Example 1 using the nicardipine-enhancer gel formulation.

As with the previous examples, the peel force between the PIB adhesive and the release liner is greater than the force necessary to break the peelable seal between the microporous membrane and the peelable disc. As such, the peelable disc is removed with the release liner when the release liner is peeled away from the system, simultaneously creating the peripheral adhesive pattern. The in vitro skin flux from the nicardipine system is determined using the methods described above to be 15 ug/cm$^2$/hr.

Example 4

The L1 laminate is prepared as described in Example 1 using 3M #93088 medical grade acrylic adhesive in place of the silicone adhesive and a silanized release liner in place of the Akrosil Biorelease release liner.

Prior to laminating the microporous membrane, the disc is fastened to the underlying release liner by using a sewing needle with a nylon thread. The needle with the nylon thread is pushed through the disc at a distance of 0.0469 inches from its peripheral edge through the underlying adhesive and release liner. This procedure is repeated in the opposite direction by first piercing the release liner followed by the disc 0.1875 inches removed from the first stitch, while still maintaining 1 mm distance to the edge of the disc. The nylon thread is pulled tight and the two ends are tied to each other forming a knot as close to the surface of the disc as possible. This stitch forms the mechanical bond between the disc and the release liner.

The 0.002 inch thick microporous membrane (3M MSP-61588) is then laminated over the entire surface of the above peelable disc/adhesive/release liner structure to form a membrane/peelable disc/adhesive/release liner laminate. This structure is used to fabricate calcitriol, pindolol and nicardipine transdermal systems as described in Examples 1, 2 and 3.

Example 5

An L1 laminate is prepared as described in Example 4 except that a mechanical bonding of the disc to the release liner is obtained by stapling the disc to the release liner. The disc is stapled 0.030 of an inch removed from the peripheral edge of the disc to the release liner by using a 0.375 inch long metal staple. Calcitriol, pindolol and nicardipine transdermal systems are then prepared as described in Examples 1, 2 and 3.

Example 6

An L1 laminate is prepared as described in Example 4 except that the mechanical bond is obtained by the use of a plastic rivet. This rivet is formed by first punching a 0.020 inch diameter hole into the disc/ adhesive/release liner laminate. The center of this hole is 0.030 inches set back from the edge of the disc.

A thermoset polymer is then extruded into this hole and forms a mechanical bond upon cooling.

Transdermal systems are then prepared from this L1 laminate as described in the previous examples.

What is claimed is:

1. A device for administering an active agent to the skin or mucosa of an individual comprising a laminated composite of:
    (a) a backing layer;
    (b) an active agent-permeable membrane, the backing layer and membrane defining
    (c) a reservoir therebetween that contains a formulation of the active agent, said reservoir having a smaller periphery than the backing layer and membrane such that a portion of the backing layer and membrane extends outwardly of the periphery of the reservoir;
    (d) a first peelable active agent formulation-impermeable layer that underlies the reservoir and a portion of said outwardly extending portion of the backing layer and membrane;

(e) an adhesive layer that underlies and covers the first peelable active agent formulation-impermeable layer and said outwardly extending portion of the backing layer and membrane;

(f) a second peelable active agent formulation-impermeable layer that underlies and covers the adhesive layer;

(g) a permanent heat seal about the periphery of the reservoir between the backing layer and the membrane; and (h) a peelable heat seal between the membrane and the first peelable active agent formulation-impermeable layer located underneath and at a radius not less than that of the permanent heat seal, said permanent and peelable heat seals providing barriers to migration of components of the active agent formulation from the reservoir into the adhesive layer and said first and second peelable active agent impermeable layers being bonded together such that when the second peelable layer is removed from the device the peelable heat seal is broken and the first peelable layer and underlying portion of the adhesive layer is removed therewith.

2. The device of claim 1 wherein the adhesive is incompatible with one or more of the components of the formulation that permeate through the membrane to the skin or mucosa.

3. The device of claim 1 wherein the backing layer is a laminated composite of at least one layer that is impermeable to the formulation and an inner heat-sealable layer.

4. The device of claim 1 wherein the adhesive is an acrylic adhesive, the active agent is pindolol hydrochloride, and the formulation includes ethyl alcohol and glycerol monooleate.

5. The device of claim 1 wherein the adhesive is an acrylic adhesive, the active agent is nicardipine hydrochloride, and the formulation includes ethyl alcohol and glycerol monooleate.

6. The device of claim 1 wherein the adhesive is a silicone adhesive, the active agent is calcitriol and the formulation includes ethanol, methyl laurate, and water.

* * * * *